United States Patent
Cox

(10) Patent No.: US 7,051,393 B2
(45) Date of Patent: May 30, 2006

(54) METHOD AND APPARATUS FOR REMOVING DIRT AND GERMS FROM A PERSON'S SHOES BEFORE THEY ENTER A HOME OR BUSINESS

(76) Inventor: Alvin Emison Cox, 10612 Humbletonian Pl., Santa Ana, CA (US) 92705

(*) Notice: Subject to any disclaimer, the term of this patent is extended or adjusted under 35 U.S.C. 154(b) by 0 days.

(21) Appl. No.: 10/411,188

(22) Filed: Apr. 11, 2003

(65) Prior Publication Data

US 2004/0200502 A1 Oct. 14, 2004

(51) Int. Cl.
*A47L 23/02* (2006.01)

(52) U.S. Cl. .................................. 15/30; 15/36; 15/215
(58) Field of Classification Search ................ 422/300; 15/97.2, 103.5, 36, 21.1, 215–217, 37, 30, 15/32–35, 97.5
See application file for complete search history.

(56) References Cited

U.S. PATENT DOCUMENTS

| | | | | | |
|---|---|---|---|---|---|
| 3,641,609 A | * | 2/1972 | Hansen | ......................... | 15/112 |
| 4,014,060 A | * | 3/1977 | Taylor | ............................ | 15/36 |
| 5,881,427 A | * | 3/1999 | Offner | .......................... | 15/215 |
| 5,996,160 A | * | 12/1999 | Pruitt | ....................... | 15/104.92 |
| 2004/0078909 A1 | * | 4/2004 | Coppa | ..................... | 15/104.92 |

* cited by examiner

*Primary Examiner*—John Kim
*Assistant Examiner*—Laura C Cole
(74) *Attorney, Agent, or Firm*—TraskBritt

(57) ABSTRACT

This invention teaches both the means and the method for removing dirt and germs from a person's shoes before they enter a home or business. The invention uses four systems. The first system provides the method for initiating and replenishing fluids that contains a disinfectant. The second system presents the method of providing a new dampened wiping surface each time the device is ready for use. The third system provides a means of removing solid particulants from the wiping surface after it has been used. The fourth system provides the method of collecting the previously removed solids.

5 Claims, 3 Drawing Sheets

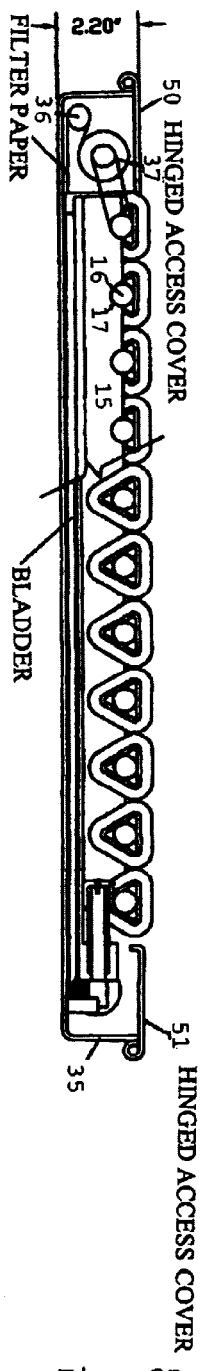
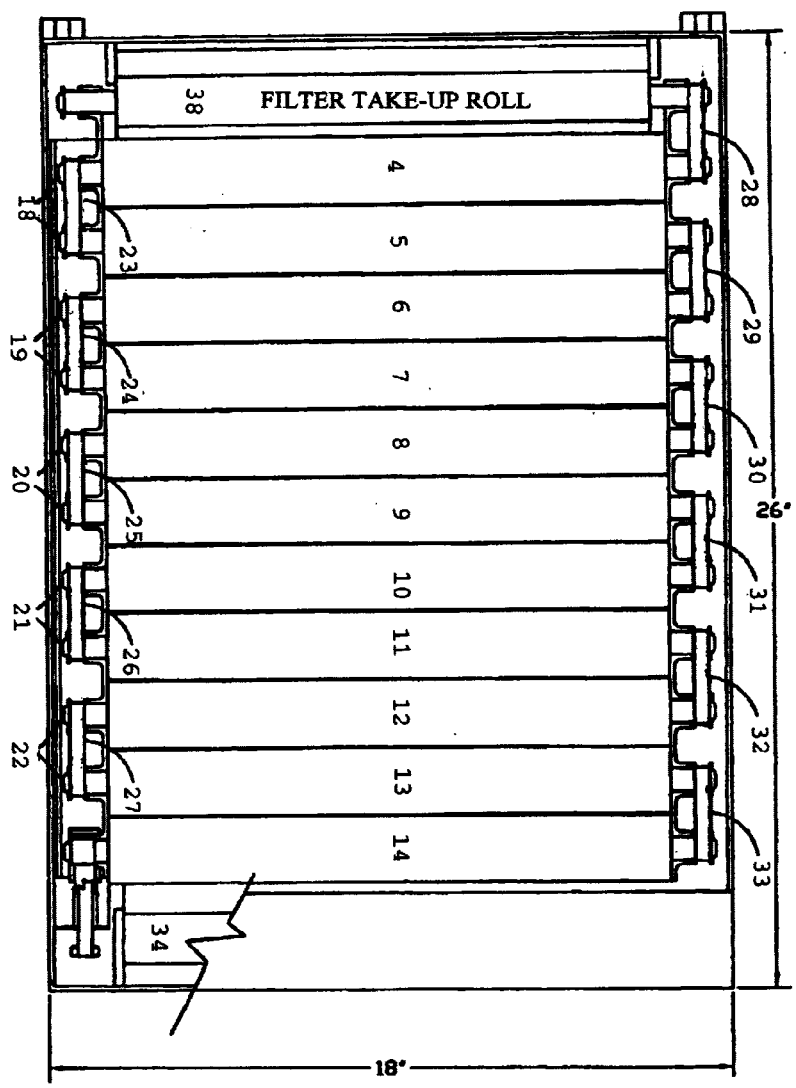
Fig. 2B
Fig. 2A

READY FOR USE

IN USE

RESET ACTION BEGINNING

METHOD AND APPARATUS FOR REMOVING DIRT AND GERMS FROM A PERSON'S SHOES BEFORE THEY ENTER A HOME OR BUSINESS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Currently, dirt and germs are carried into a home or business on the soles of shoes. In many cultures, people are trained to remove their shoes at the entrance. Where this custom is not practiced, a major concern of parents is the resultant potential harm to the health of their very young children. The danger to health is as a result of their child's contact with tracked in dirt and germs. To overcome this problem they feel it is necessary to clean and vacuum floors and carpets frequently. Cost of cleaning equipment and materials such as vacuum cleaners, steam cleaners, mops, brooms chemical cleaners and disinfectants, is significant. It becomes apparent that removal of these harmful and messy contaminants takes a lot of time and money.

It became obvious that a method was needed to clean the soles of shoes on anyone prior to their entry in order to get rid of dirt and germs before they can be tracked into the home.

The method contemplated required four systems. The first system would provide the method of initiating and replenishing the necessary cleaning fluids containing a disinfectant. The second to be a method of presenting a dampened wiping surface each time the device was to be used. The third to be a means of removing solid particulants from the wiping surface, and the fourth to be a method for collecting the previously removed solids.

Other considerations during the development of this invention involved production cost, environmental effects, and skill required using it.

Another consideration during the development of this invention was that it should include the means of accommodating several optional sizes and shape of segments. This feature would permit acceptance by a diverse group of users. For example, the reservoir tray could be sized differently for commercial or residential applications. The capacity of the contaminant collection system could be altered yet still be compatible with the basic components. The disinfectant strength of cleansing fluid could be changed during the "flu" season.

Several commercially available, water soluble, disinfectants arc available. The chemicals used must have the ability to dissolve completely, have very long shelf life in solution, and not leave any residue on any commercially available material used for the soles of shoes. Further, only those chemicals that will be used must have been accepted as being environmentally compatible.

The packaging method, which is a necessary concept of this invention, involves pre-mixing of the disinfectant with distilled water. The resultant solution should be packaged in standard pint, quart, and half-gallon units. The only skill required of the user should be to pour enough pre-mixed solution anywhere on the wiping area to fill the reservoir to a visible marker.

The shape and physical dimensions of the wiping surface for this invention must be developed to be compatible with a majority of shoe types, user weights, and shoe sizes.

The design for this invention should lend itself to economical high volume production means.

The unique design features should provide for easy use in the field.

BRIEF SUMMARY OF THE INVENTION

The system of initiating and replenishing the cleaning fluids.

The system for initiating and replenishing the cleaning fluids involves methods of mixing them, packaging them, and introducing them into the device.

Pre-mixing is the preferred method. The resulting mixture will be consistent and uniform. It was decided that offering the option of having the user mix the chemicals could result in unacceptable conditions.

Packaging in standard size units, such as pints, quarts, and half gallons is the preferred method. The format is commonly accepted for most liquid type products.

Introduction of the fluids into the device is direct by pouring the solution anywhere on the wiping area to fill the reservoir to a visible reference point. This preferred method avoids the need for separate caps while providing a large pouring area, reducing potential for spillage.

The visible reference point marking the preferred reservoir level is the top of the wiping surface drive belts.

The system of presenting a dampened wiping surface each time the device is used.

Triangular shaped wiping surface components are rotated after each consecutive use. This action is initiated by means of a spring loaded trigger that is cocked when someone steps on the sole cleanser. When the user steps off of the sole cleanser, the trigger releases a driver rod connected to a series of interconnected triangular members. The motion is mechanically limited to cause exactly 120 degrees rotation of the triangular components. As a result, two of the three sides of the triangular shaped wiping surface components are always immersed in the cleaning fluid. The exposed surface has been wetted by the previous cycle. The exposed surface remains damp by wicking action. Excess retained fluid drains back into the reservoir.

The system of removing solid particulants from the wiping surface.

The two sides of the wiping surface components immersed in the cleaning fluid have trapped particles of dirt. As a result of the weight of these particles, they will fall out of the carpet like material and move to the bottom of the reservoir. The exposed wiping surface collects the dirt particles when the device is used immediately after use, the wiping surface has automatically been rotated into the fluid before the dirt has had an opportunity to become embedded in the fibers of the carpet material. Intervals between cycles is significantly greater than the time the device is used to clean the soles of a shoe. As a result, the time available for fall out of the dirt particles is of considerable magnitude since it equals the duration between two complete cycles.

System for collecting removed solids.

A clean roll of filter paper is located at the end of the device. It is placed such that when unrolled, the web of the material is towards the bottom of the reservoir surface. The end of the roll is unwound and passed the full length of the reservoir where it is then attached to a take up roll. The take up roll is mechanically connected to the wiping surface components by means of a flat belt. As a result, the filter material moves a distance equal to that traveled by a point on the outer surface of the take up roll during a 120-degree rotation. In the preferred embodiment this averages ⅝ of an inch.

Dirt particles that have fallen free of the wiping surface of the carpet surface collect on the filter paper.

The dirt particles trapped on the filter paper are moved on to the take up roll. In the preferred embodiment, the old roll will require replacement approximately every 300 cycles.

BRIEF DESCRIPTION OF THE SEVERAL VIEWS OF THE DRAWINGS

The drawings illustrate the preferred embodiment for a residential application. It is obvious that other sizes for commercial applications would be similar, varying only in dimensional scale.

This figure describes the physical shape of the wiping surface assembly and its components for the preferred embodiment.

FIG. 2A is a top plan view of a preferred embodiment of an apparatus for removing dirt and germs from a person's shoes according to the invention.

FIG. 2B is a side view of the apparatus shown in FIG. 2A.

These figures show the relationship of all of the components to each other.

Figure 3A:
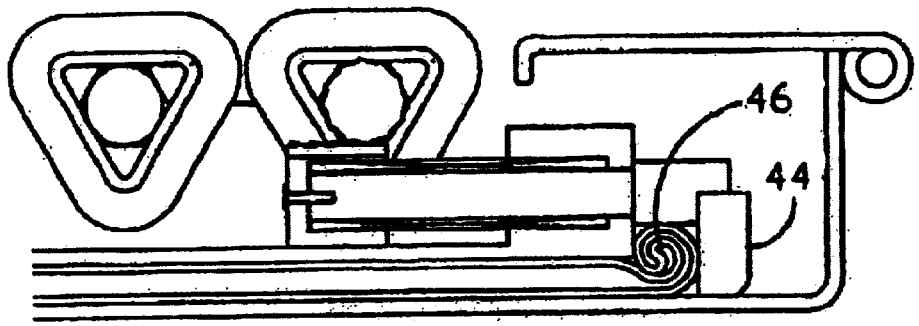

FIG. 3A is a cross-sectional partial side view of the apparatus shown in FIG. 2A and FIG. 2B.

This figure shows the relationship of the "trigger", the actuator type bladder, and the wiping surface when the unit ready for use.

Figure 3B:
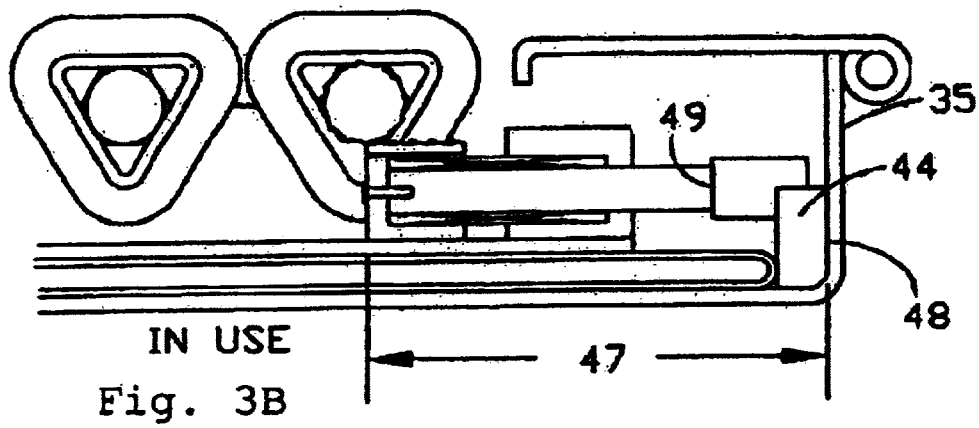

FIG. 3B is a cross-sectional partial side view like that of FIG. 3A showing the relationship of components when the system is in use.

Figure 3C:
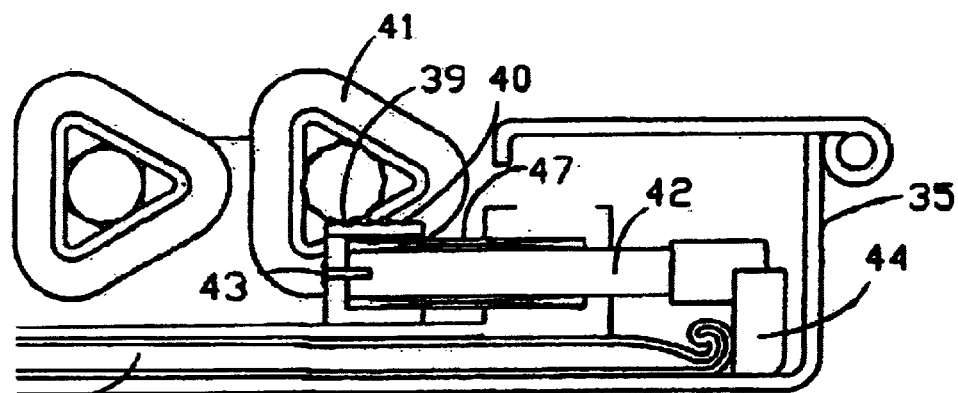

FIG. 3C is a cross-sectional partial side view like that of FIG. 3A illustrating the relationship of components as the reset action is beginning.

DETAILED DESCRIPTION OF THE INVENTION

Figure 1A:
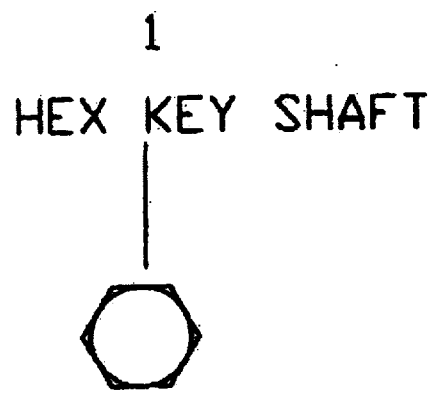
FIG. 1A is an end view of a hex key central shaft.
Figure 1B:
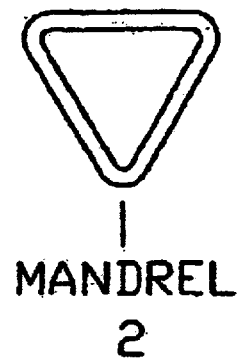
FIG. 1B is an end view of a triangular mandrel.
Figure 1C:
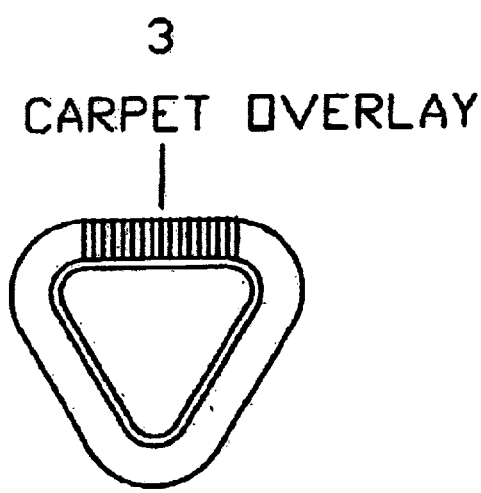
FIG. 1C is an end view of the triangular mandrel shown in FIG. 1B having a carpet overlay.
Figure 1D:
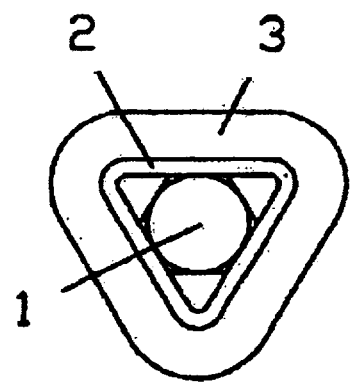
FIG. 1D is an end view of a wiping surface assembly that includes the hex key shaft shown in FIG. 1A and the triangular mandrel having a carpet overlay shown in FIG. 1C.

Refer to FIG. 1D, a drawing of one of the wiper assemblies. A central shaft made from key stock with round bearing end journals (1) is inserted into triangular mandrel (2). A carpet overlay (3), made by butt seaming a cylindrical segment, is slipped tightly onto the triangular mandrel (2).

In the preferred embodiment, shown in FIGS. 2A–2B, eleven assemblies (4) through (14) are placed in receptacle tray (15) with typical shaft ends (16) sitting in bearing half round zone (17) et al. Alternating pairs of roller assemblies (18) through (22) are connected by flat belts (23) through (27) on one side, beginning with roller assembly (4); and, by flat belts (29) through (33) on the opposite side beginning with roller assembly (5). The purpose of this method of connection is to rotate each roller assembly at the same time and by the same amount.

A filter roll made of lightweight waterproof paper like material (34) is placed in outer tray (35). The filter paper is connected around idler roller (36) and in turn to take up roller (37). In this position, any offal from soles of shoes is collected and rolled onto an easily removed disposable piece (38).

Assembly (14) has a one way clutch sprag profile (39) shown in FIGS. 3A–3C. A connecting horizontally sliding member (40) has opposing sprags (41). Horizontally sliding member (40) is connected to stepped shaft (42) by screw (43). Stepped shaft (42) is welded to reaction member (44), which is slideable on the bottom of outer tray (35). A fluid filled bladder tube (45) is placed between receptacle tray (15) and outer tray (35). A coil end (46) of fluid filled bladder tube (45) is biased by a flat spring (not shown) to assume a coil shape whenever the unit is ready for use. When this device is in use, a persons weight results in downwards movement on the fluid filled bladder tube (45) resulting in fluid flowing into the coil end (46) causing it to unroll and push reaction member (44) into contact with the inner wall of outer tray (35). When the user steps off of the device, the bladder returns to its earlier preset position as a result of spring (47). The combined action will only result in rotation of the roller assemblies when the person steps off of the device; but not when stepping on to the device. This assembly is narrow, being no greater than 1.00". The length and width of the bladder are designed such that a fraction 1/16" vertical movement will result in a ⅝" movement of the sprag driver assembly (52). Total motion is controlled by stops (48) and (49) to be precisely 120 degrees for each use cycle.

Assembly sequence starts with placement of fluid filled bladder tube (45) into outer tray (35), followed by inserting a new filter roll (34). Filter paper from filter roll (34) is wrapped around idler roller (36) and then on to take up roller (37). Hinged access covers (50) and (51) are left in an "open" position. The previously assembled roller assemblies are then placed in position. Flat belt (28) is connected to take up roller (37). Each use moves the filter roll ⅝".

With the total assembly completed, it is filled to the top edge of the flat belts (23) to (27) and (29)–(33) with any of commercially available fast drying, disinfectant type premixed fluid. ⅔ of each roller is now immersed in the fluid. The top surface as a result of wicking action remains damp.

Hinged access covers (50) and (51) provide access to the components of this invention.

The width of 18" and the length of 26" have been determined to be the most reasonable for a person to stand on this unit and "Wipe their feet". Dirt removed from the soles of the shoes is trapped in the carpet fibers. Germs are killed by contact with the moistened carpet surface. When the person steps off the device, all rollers rotate 120 degrees. This places the roller surface most recently in contact with the shoe sole into the fluid and allows the dirt to float free of the carpet and deposit onto the filter paper. That surface remains in the fluid through one more cycle.

It will be apparent that the method and apparatus of the present invention will provide a means of cleaning the soles of a person's shoes while they are being worn. The cleaning action is accomplished efficiently and economically by users merely "wiping," their feet on the device surface. It should be understood that although the preferred method of assembling the components is unique, other methods and apparatus may be employed. Further it is understood that this invention will function as described with a variety of sizes and materials.

According to the provisions of the patent statutes, I have explained the principal, preferred construction and mode of operation of my invention and have illustrated and described what I now consider to represent its best embodiments. However, it should be understood that, within the scope of the appended claims, the invention may be practiced otherwise than as specifically illustrated and described.

What I claim as my invention:

1. An apparatus for cleansing shoes comprising:

a tray for holding cleansing fluid;

a plurality of mandrels suspended over at least a portion of the tray, each mandrel of the plurality of mandrels having at least two generally flat shoe-cleansing surfaces, each mandrel of the plurality of mandrels being coupled to adjacent mandrels of the plurality of mandrels, rotation of one mandrel causing equal rotation of each mandrel of the plurality of mandrels, the plurality of mandrels being aligned to provide a substantially flat shoe-cleansing platform comprising one flat shoe-cleansing surface of each mandrel of the plurality of mandrels; and a mechanism configured to store energy when a user steps onto the plurality of mandrels and to release the stored energy when the user steps off from the plurality of mandrels, the mechanism being configured to rotate each mandrel of the plurality of mandrels each time stored energy is released.

2. An apparatus for cleansing shoes as recited in claim 1, wherein the mechanism is configured to rotate each mandrel of the plurality of mandrels through a predetermined angle each time stored energy is released.

3. An apparatus for cleansing shoes as recited in claim 1, wherein each mandrel of the plurality of mandrels is triangular providing three generally flat shoe-cleansing surfaces.

4. An apparatus for cleansing shoes as recited in claim 3, wherein the mechanism is configured to rotate each mandrel of the plurality of mandrels through an angle of 120 degrees each time stored energy is released.

5. An apparatus for cleansing shoes as recited in claim 1, further comprising:

a roll of filter paper positioned at a first end of the tray; and a take up roller positioned at an opposite end of the tray, the take up roller being coupled to at least one mandrel of the plurality of mandrels, the take up roller rotating upon rotation of the at least one mandrel, the take up roller being configured to pull and collect filter paper from the roll of filter paper, the filter paper passing beneath the plurality of mandrels upon rotation of the at least one mandrel.

* * * * *